US011899026B2

(12) United States Patent
Refaai et al.

(10) Patent No.: US 11,899,026 B2
(45) Date of Patent: Feb. 13, 2024

(54) ABO BLOOD GROUP POINT-OF-CARE CHIP TESTING

(71) Applicants: University of Rochester, Rochester, NY (US); Rochester Institute of Technology, Rochester, NY (US)

(72) Inventors: Majed J. Refaai, Henrietta, NY (US); Steven W. Day, Rochester, NY (US)

(73) Assignee: University of Rochester, Rochester Institute of Technology, Rochester, NY (US)

( * ) Notice: Subject to any disclaimer, the term of this patent is extended or adjusted under 35 U.S.C. 154(b) by 682 days.

(21) Appl. No.: 17/065,002

(22) Filed: Oct. 7, 2020

(65) Prior Publication Data

US 2021/0102962 A1  Apr. 8, 2021

Related U.S. Application Data

(60) Provisional application No. 62/911,708, filed on Oct. 7, 2019.

(51) Int. Cl.
*G01N 33/80* (2006.01)
*G01N 33/53* (2006.01)

(52) U.S. Cl.
CPC ......... *G01N 33/80* (2013.01); *G01N 33/5302* (2013.01)

(58) Field of Classification Search
CPC ............................ G01N 33/80; G01N 33/5302
See application file for complete search history.

(56) References Cited

U.S. PATENT DOCUMENTS

| 4,178,071 | A | 12/1979 | Asbell |
| 9,686,395 | B2 | 6/2017 | Erickson |
| 10,857,301 | B2 | 12/2020 | Loonan |
| 2009/0170062 | A1 | 7/2009 | Schwind |
| 2010/0112723 | A1* | 5/2010 | Battrell ............ B01L 3/502746 422/68.1 |
| 2013/0017623 | A1 | 1/2013 | Wu |
| 2016/0206818 | A1 | 7/2016 | Berend |
| 2018/0256818 | A1 | 9/2018 | Lümkemann |
| 2021/0373007 | A1 | 12/2021 | Refaai |

FOREIGN PATENT DOCUMENTS

| DE | 19713249 A1 | 10/1998 |
| DE | 10311731 | 10/2003 |
| KR | 20170006981 A | 1/2017 |

(Continued)

OTHER PUBLICATIONS

Karimi, Shadi, et al. "A passive portable microfluidic blood-plasma separator for simultaneous determination of direct and indirect ABO/Rh blood typing." Lab on a Chip 19.19 (2019): 3249-3260. (Year: 2019).*

(Continued)

*Primary Examiner* — Robert J Eom
(74) *Attorney, Agent, or Firm* — Riverside Law LLP

(57) ABSTRACT

The present invention provides point-of-care blood typing devices. The devices require only a small sample of blood and are able to provide results within minutes. The devices are capable of identifying A, B, AB, and O type blood. The devices are also capable of identifying blood that is positive (+) or negative (−) for the D antigen.

19 Claims, 5 Drawing Sheets

(56) References Cited

FOREIGN PATENT DOCUMENTS

| TW | 201336537 A | 9/2013 |
|---|---|---|
| WO | 8603008 | 5/1986 |
| WO | 9009596 | 8/1990 |
| WO | 2013083619 | 6/2013 |
| WO | 2019195710 A1 | 10/2019 |

OTHER PUBLICATIONS

Ashiba, Hiroki, et al. "Microfluidic chips for forward blood typing performed with a multichannel waveguide-mode sensor." Sensing and bio-sensing research 7 (2016): 121-126.

Chen, Jun-You, et al. "Rapid and inexpensive blood typing on thermoplastic chips." Lab on a Chip 15.24 (2015): 4533-4541.

Li, Miaosi, et al. "Paper-Based blood typing device that reports patient's blood type "in writing"." Angewandte Chemie 124.22 (2012): 5593-5597.

Lilly (Disposable Insulin Delivery Device User Manual, 2005). (Year: 2005).

Malomgre et al (Recent and future trends in blood group typing, Anal Bioanal Chem (2009) 393:1443-1451) (Year: 2009).

Wessel, Lindzi. "Watch a Special Paper Tool That Can Determine Your Blood Type in Seconds." Science, American Association for the Advancement of Science, Mar. 15, 2017, www.science.org/content/article/watch-special-paper-tool-can-determine-your-blood-type-seconds. Accessed Sep. 25, 2023.

Zhang, Hong, et al. "A dye-assisted paper-based point-of-care assay for fast and reliable blood grouping." Science translational medicine 9.381 (2017): eaaf9209.

\* cited by examiner

ABO BLOOD GROUP POINT-OF-CARE CHIP TESTING

CROSS-REFERENCE TO RELATED APPLICATIONS

This application claims the benefit of priority under 35 U.S.C. § 119(e) to U.S. Provisional Patent Application No. 62/911,708, filed Oct. 7, 2019, the contents of which are incorporated by reference herein in its entirety.

BACKGROUND OF THE INVENTION

The principle of the blood group system (also known as the ABO system) is the presence or absence of specific antigens that are physically exposed on the red blood cell (RBC) membrane. Two main antigens play an important role in differing blood groups in humans, the A and B antigens. Depending on gene expression, individuals exposing either antigen are marked as group "A" or group "B", respectively; individuals exposing both antigens are identified as group "AB"; and individuals missing both antigens are known as group "O". The carbohydrate structure of antigen A and B are slightly different, which stimulates antibody formation to the missing antigen or antigens early in life. Thus, individuals of group "A", for instance, will have anti-B antibodies circulating in their plasma, and vice versa for individuals of group "B". While individuals of group "AB" exhibit neither antibody, group "O" individuals develop both antibodies.

Identification of the ABO group system is essential in blood transfusions since exposure to inappropriate antibodies can cause acute RBC hemolysis that may lead to significant consequences, such as acute renal failure and death. ABO group identification is simple and can be performed within 20-25 minutes in the presence of adequate laboratory techniques. However, such a delay in management of acutely bleeding patients may be significantly harmful. Therefore, administration of group "O" RBCs (so-called "universal donor") until the patient's ABO group is identified is a common transfusion practice worldwide.

While administration of group "O" RBCs to all trauma patients is a presumably safe practice, the amount of anti-A and anti-B antibodies administered with each unit (30-70 mL of plasma) can cause RBC hemolysis of any non-group "O" patients (about 50-55% of the U.S. population). Significant complications have been reported following administration of the O group RBCs to non-O group recipients. This is usually due to the anti-A and anti-B antibodies present in the plasma included in the RBC unit and their interactions with A or B antigens present on the RBC membrane. Furthermore, anti-AB antibodies can also form immune complexes with the circulating soluble A and B antigens that can further contribute to considerable harm of different tissue in addition to RBC hemolysis.

Early identification of a patient's blood group will allow ABO identical transfusion and reduce exposure to anti-AB antibodies and formation of harmful immune complexes. Of note, in addition to the ABO group, the presence or absence of another antigen that only exists on the RBC membrane, known as the "D" antigen, is very essential in blood transfusion.

There is a need in the art for an improved point-of-care blood typing device. The present invention meets this need.

SUMMARY OF THE INVENTION

In one aspect, the present invention relates to a portable blood typing device comprising: a body having an exterior surface; a port formed in the exterior surface of the body; one or more microchannels embedded in the body, each microchannel extending from the port to an air hole formed in the exterior surface of the body; and one or more reservoirs embedded in the exterior surface of the body, each reservoir being fluidly connected to each microchannel; wherein the fluid connection between each reservoir and each microchannel is obstructed by a breakable seal.

In one embodiment, a first reservoir connected to a first microchannel contains a fluid composition comprising a first probe that binds to antigen A, a second reservoir connected to a second microchannel contains a fluid composition comprising a second probe that binds to antigen B, and a third reservoir connected to a third microchannel contains a fluid composition comprising a third probe that binds to antigen D. In one embodiment, the first probe is anti-A antibody, the second probe is anti-B antibody, and the third probe is anti-D antibody. In one embodiment, a fourth reservoir connected to a fourth microchannel contains a fluid selected from the group consisting of: gas, air, water, saline, and phosphate buffered saline.

In one embodiment, each breakable seal is selected from the group consisting of: a foil, a plastic film, a plastic ampoule, and a glass ampoule. In one embodiment, each breakable seal is breakable by applying pressure to a respective reservoir. In one embodiment, each breakable seal is breakable by a needle or blade.

In one embodiment, the body is at least partially transparent. In one embodiment, the device further comprises one or more magnifying lenses positioned adjacent to a microchannel downstream from a reservoir. In one embodiment, the device further comprises one or more light sources positioned adjacent to a microchannel downstream from a reservoir. In one embodiment, the device further comprises a blood typing chart attached to the body, the blood typing chart assigning a positive reading based on agglutination in a microchannel downstream from a reservoir and a negative reading based on the absence of agglutination in a microchannel downstream from a reservoir. In one embodiment, the device further comprises a sensor electronically connected to a CPU and a display, wherein the sensor automatically detects a positive or negative signal in each microchannel downstream from a reservoir, the CPU assigns a blood type based on the detected signals, and the display shows the blood type. In one embodiment, the sensor is selected from the group consisting of: a light sensor, an impedance sensor, and a color sensor.

In another aspect, the present invention relates to a method of blood typing, comprising the steps of: providing the portable blood typing device of the present invention; injecting a blood sample into the port; rupturing each of the breakable seals; and recording the presence of agglutination in each microchannel downstream from a reservoir.

In one embodiment, the presence of agglutination in a first microchannel downstream from a first reservoir containing a fluid composition comprising a first probe that binds to antigen A and the absence of agglutination in a second microchannel downstream from a second reservoir containing a fluid composition comprising a second probe that binds to antigen B indicates that the blood sample comprises A-type blood.

In one embodiment, the absence of agglutination in a first microchannel downstream from a first reservoir containing a fluid composition comprising a first probe that binds to antigen A and the presence of agglutination in a second microchannel downstream from a second reservoir containing a fluid composition comprising a second probe that binds to antigen B indicates that the blood sample comprises B-type blood.

In one embodiment, the presence of agglutination in a first microchannel downstream from a first reservoir containing a fluid composition comprising a first probe that binds to antigen A and the presence of agglutination in a second microchannel downstream from a second reservoir containing a fluid composition comprising a second probe that binds to antigen B indicates that the blood sample comprises AB-type blood.

In one embodiment, the absence of agglutination in a first microchannel downstream from a first reservoir containing a fluid composition comprising a first probe that binds to antigen A and the absence of agglutination in a second microchannel downstream from a second reservoir containing a fluid composition comprising a second probe that binds to antigen B indicates that the blood sample comprises O-type blood.

In one embodiment, the presence of agglutination in a third microchannel downstream from a third reservoir containing a fluid composition comprising a third probe that binds to antigen D indicates that the blood sample comprises Rh positive blood.

In one embodiment, the absence of agglutination in a third microchannel downstream from a third reservoir containing a fluid composition comprising a third probe that binds to antigen D indicates that the blood sample comprises Rh negative blood.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

DETAILED DESCRIPTION

The present invention provides point-of-care blood typing devices and methods of use. The devices require only a small sample of blood and are able to provide results within minutes. The devices are capable of identifying A, B, AB, and O type blood. The devices are also capable of identifying blood that is positive (+) or negative (−) for the D antigen.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Blood Typing Device

Figure 1:
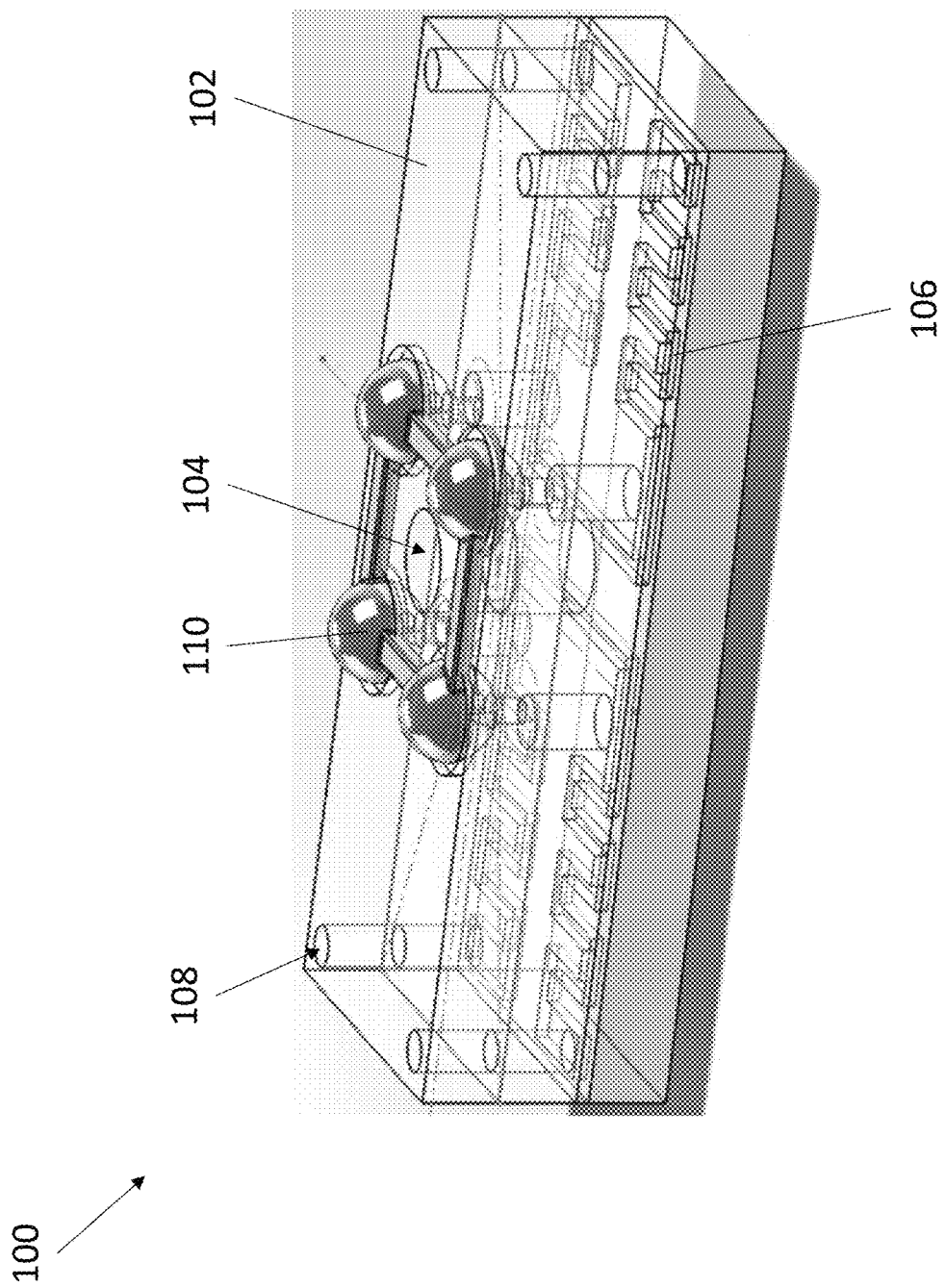
FIG. 1 depicts a perspective view of an exemplary blood typing device.
Figure 2:
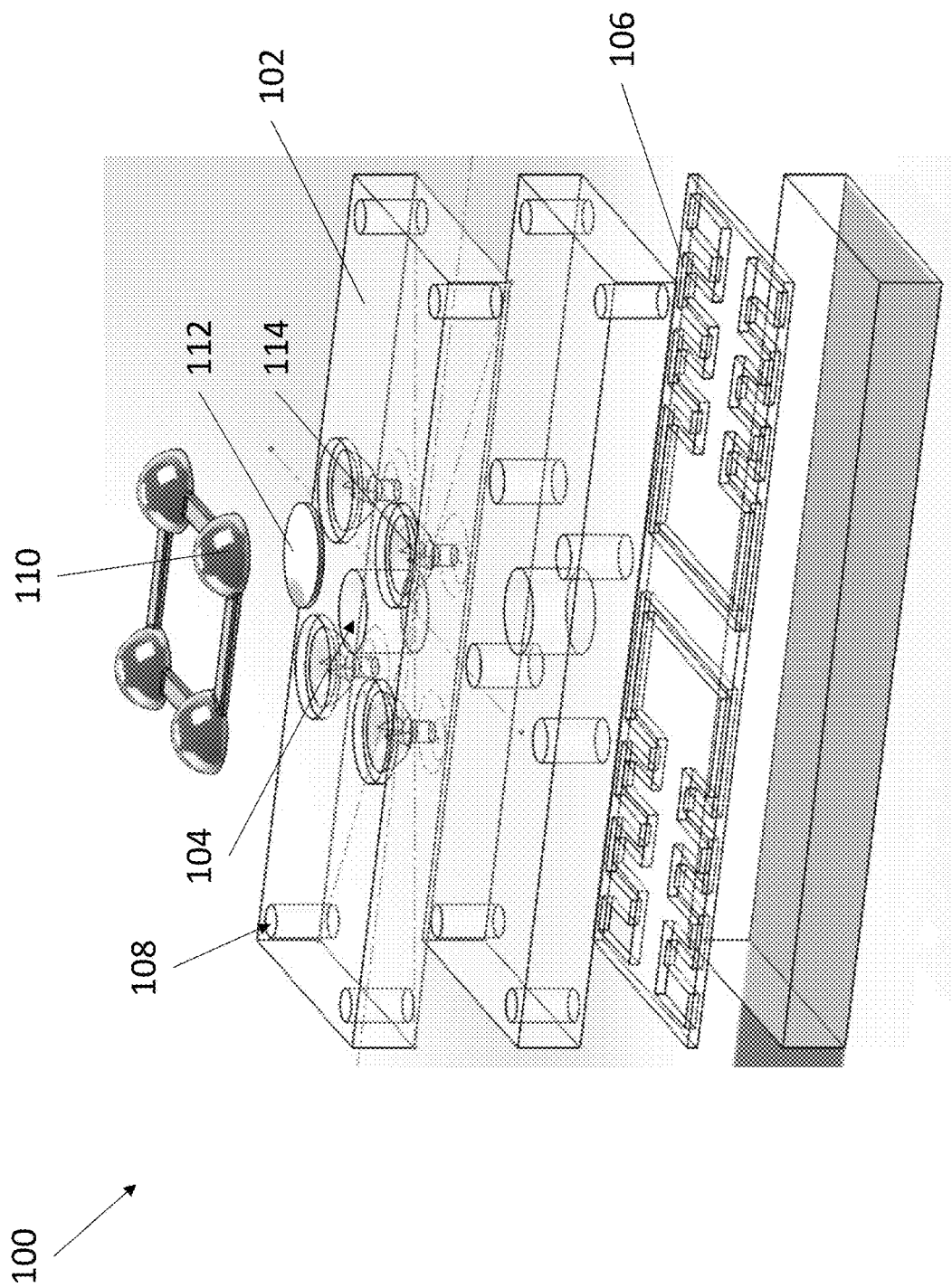
FIG. 2 depicts an exploded perspective view of an exemplary blood typing device.

Referring now to FIG. 1 and FIG. 2, an exemplary blood typing device 100 is depicted. Device 100 comprises a body 102, a port 104, at least one microchannel 106, at least one air hole 108, at least one reservoir 110, and at least one breakable seal 112. Body 102 can have a solid or hollow construction with a solid exterior surface. Port 104 is an aperture formed in the exterior surface of body 102 and extends into the interior of body 102 to form a well. In some embodiments, port 104 is closeable, such as by a cap or plug. In some embodiments, port 104 can include one or more connectors, including but not limited to a luer lock, a tapered connector, a threaded connector, and the like. Body 102 can be fully or partially transparent to enable visualization of internal components.

Similar to port 104, each air hole 108 is an aperture formed in the exterior surface of body 102 and extends into the interior of body 102 to form a well. Each air hole 108 is fluidly connected to port 104 by a microchannel 106 embedded within body 102. In this manner, a fluid placed within port 104 flows through each connected microchannel 106 by way of capillary action, wherein each air hole 108 connected to each microchannel 106 permits air within each microchannel 106 to evacuate to promote the movement of the fluid through each microchannel 106.

As described above, each microchannel 106 is formed by a lumen that extends between port 104 and an air hole 108. Each microchannel 106 can have any suitable size and shape. For example, microchannel 106 can have any desired cross-sectional shape, including but not limited to circular, ovoid, square, rectangular, triangular, and the like. Microchannel 106 can have any desired length. In some embodiments, microchannels 106 can each have a serpentine or circuitous path to maximize length within body 102.

Figure 3:
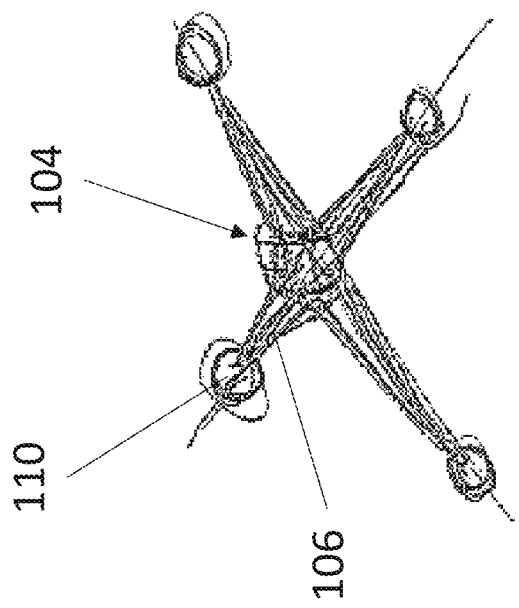
FIG. 3 depicts various reservoir configurations.
Figure 3:
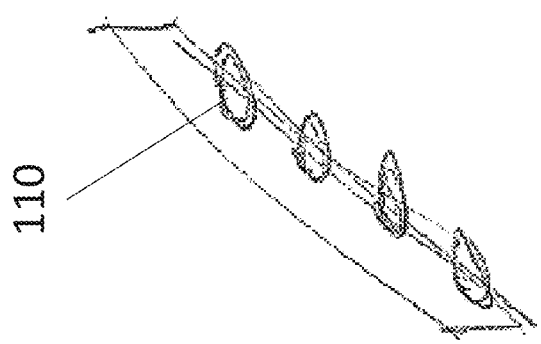

Reservoir 110 is an enclosed container having a hollow interior for storing a liquid or lyophilized probe or capture agent composition. In various embodiments, reservoir 110 is airtight and watertight such that the contents of its hollow interior can be stably stored for an extended period of time with little to no change in compositional makeup. Reservoir 110 can also store a control composition, such as a gas, air, sale, water, and phosphate buffered saline. In some embodiments, reservoir 110 is prepackaged with device 100 and integrated into body 102. In some embodiments, reservoir 110 is provided separately from device 100 and loadable onto body 102 prior to use. The one or more reservoirs 110 can be arranged in any desired pattern, including but not limited to a linear array (FIG. 3, left) and an X array (FIG. 3, right).

Device 100 can be provided with any number of different reservoirs 110, each reservoir 110 holding a different probe or capture agent composition. The probes or capture agents can be any suitable molecule, including antibodies, antigens, proteins, and nucleic acids. The probes or capture agents can be configured to capture any desired molecule, including proteins, amines, peptides, antigens, antibodies, nucleic acids, steroids, eicosanoids, DNA sequences, RNA sequences, bacteria, viruses, and fragments thereof. For example, in some embodiments, a first reservoir connected to a first microchannel contains a fluid composition comprising a first probe that binds to antigen A (such as an anti-A antibody), a second reservoir connected to a second microchannel contains a fluid composition comprising a second probe that binds to antigen B (such as an anti-B antibody), and a third reservoir connected to a third microchannel contains a fluid composition comprising a third probe that binds to antigen D (such as an anti-D antibody). In some embodiments, the probes or capture agents can employ mechanical means for capturing particles, such as magnetic beads for capturing ferromagnetic particles, ferromagnetic beads for capturing magnetic particles, or nanohairs tuned for capturing particles and nanoparticles within a particular size range. In some embodiments, the one or more microchannels 106 can each have a surface treatment comprising a probe or capture agent. The one or more microchannels 106 can thereby be suitable for capturing any particle of interest for detection and/or analysis. The various probes or capture agents can be provided in any suitable amount. For example, each reservoir 110 can comprise an amount of a probe or capture agent between about 10 µL and 100 µL. The various probes or capture agents can be provided in any suitable concentration. For example, anti-A antibodies can be provided at a titer of 1:64, anti-D antibodies can be provided at a titer of 1:32, and anti-B antibodies can be provided at a titer of 1:64.

Device 100 comprises at least one reservoir 110 fluidly connectable to each microchannel 106, wherein a fluid connection between each reservoir 110 and each microchannel 106 is obstructed by a breakable seal 112 (visible in FIG. 2). The term "fluidly connectable" is meant to describe that a reservoir 110 connected to a microchannel 106 permits the contents of reservoir 110 to flow into microchannel 106, but with the addition of breakable seal 112 obstructing the connection, the contents of reservoir 110 are prevented from flowing into microchannel 106. In this manner, the contents in a reservoir 110 are isolated from a connected microchannel 106 by a breakable seal 112 until a user chooses to rupture breakable seal 112, thereby introducing the contents of reservoir 110 into microchannel 106.

Figure 4:
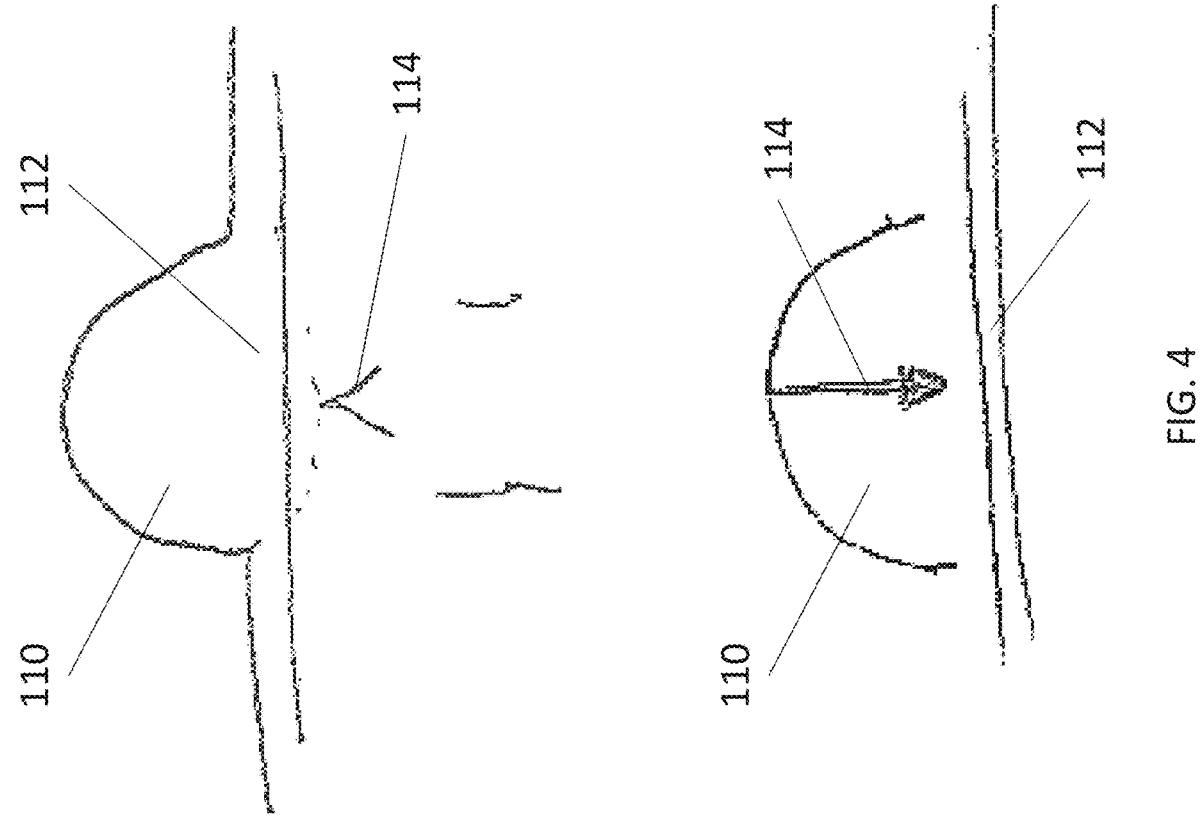
FIG. 4 depicts various reservoir orientations.

Breakable seal 112 can be ruptured in any suitable manner. In certain embodiments, the method by which breakable seal 112 is ruptured depends upon the construction of reservoir 110. For example, in some embodiments reservoir 110 is a pliable plastic container and breakable seal 112 is constructed from a tearable material, including but not limited to foil or a plastic film, similar to blister packaging of pills contained in flexible plastic housings and sealed with a brittle backing. Applying an external source of pressure on reservoir 110 increases the pressure of the interior of reservoir 110, causing breakable seal 112 to tear and release the contents of reservoir 110 into microchannel 106. In some embodiments, breakable seal 112 is integrated into reservoir 110. For example, reservoir 110 can take the form of a glass or plastic ampoule and breakable seal 112 can take the form of a weakened portion of the ampoule, such as a notch, scoring, or thin walled region. Applying an external source of pressure on reservoir 110 thereby leads to a controlled rupturing of reservoir 110 along breakable seal 112. In some embodiments, device 100 further comprises one or more piercing elements 114 to rupture breakable seal 112, such as a needle or blade. Piercing elements 114 can be positioned below a breakable seal 112, such that applying an external source of pressure on reservoir 110 pushes a breakable seal 112 against the tip of a piercing element 114, thereby rupturing breakable seal 112 (visible in FIG. 2 and FIG. 4, top). Piercing elements 114 can also be positioned within a reservoir 110, such that applying an external source of pressure on reservoir 110 pushes a piercing element 114 against a breakable seal 112, thereby rupturing breakable seal 112 (visible in FIG. 4, bottom). In various embodiments, device 100 can include a frame, plate, or button that, when pressed, applies equal pressure on all or a selection of reservoirs 110 at the same time for ease of use and consistency in timing.

Figure 5:
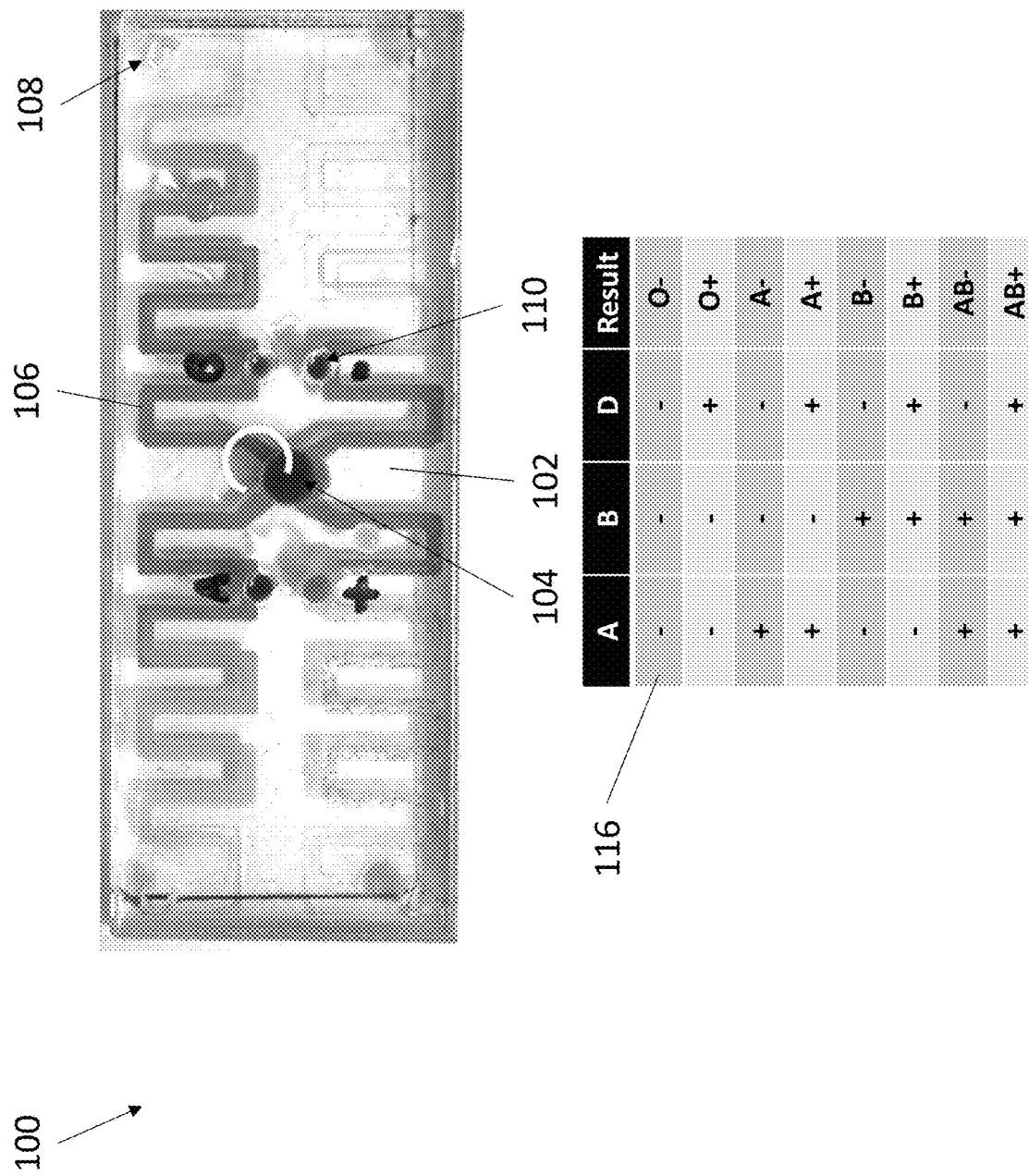
FIG. 5 depicts a top-down view of a prototype blood typing device (top) and a blood typing reference chart (bottom).

Referring now to FIG. 5, blood typing device 100 is depicted with a blood sample deposited into port 104. It should be understood that while a blood sample is described herein, device 100 is not limited to the analysis of blood. Rather, device 100 is capable of accepting any suitable fluid sample, including but not limited to samples of biological origin, such as saliva, lymph, cerebrospinal fluid, mucus, urine, sweat, and the like, as well as samples of nonbiological origin, such as water samples, rain samples, and chemical compositions. In FIG. 5, a blood sample has been deposited into port 104, a liquid composition comprising anti-A antibodies has been deposited into the top left reservoir 110, a liquid composition comprising anti-B antibodies has been deposited into the top right reservoir 110, a liquid composition comprising anti-D antibodies has been deposited into the bottom left reservoir 110, and a control solution comprising saline has been deposited into the bottom right reservoir 110. The top left microchannel 106 is thereby configured to exhibit the results of binding to red blood cells (RBCs) expressing A antigens, the top right microchannel 106 configured to exhibit the results of binding to RBCs expressing B antigens, and the bottom left microchannel 106 configured to exhibit the results of binding to RBCs expressing Rh antigens.

Successful binding within a microchannel 106 results in agglutination of RBCs within the microchannel 106, indicating the presence of a respective blood type and a positive signal. The absence of binding within a microchannel 106 displays no agglutination, indicating the absence of a respective blood type and a negative signal. Different combinations of positive and negative signals identify the type of blood present in a blood sample, as shown in chart 116. In the depicted example in FIG. 3, the top left microchannel 106 exposed to anti-A antibodies and the top right microchannel 106 exposed to anti-B antibodies each have a negative signal, while the bottom left microchannel 106 exposed to anti-D antibodies has a positive signal. The blood sample is thereby identified as being O+ type blood. For ease of use, chart 116 can be provided with device 100, either as separate paper or electronic documentation or attached directly to device 100.

In some embodiments, device 100 can accept at least one additional fluid sample after being exposed to an initial fluid sample. The at least one additional fluid sample can include tags that can be conjugated to the captured particles of interest from the initial fluid sample. The tag can be any material having a detectable physical or chemical property. Such tags have been well-developed in the field of immunoassays and, in general, any tag useful in such methods can be applied to the present invention. Thus, a tag is any composition detectable by spectroscopic, photochemical, biochemical, immunochemical, electrical, optical, or chemical means.

Means of detecting tags are well known to those of skill in the art. Thus, for example, where the tag is a radioactive label, means for detection include a scintillation counter or photographic film as in autoradiography. Where the tag is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic tags may be detected by providing appropriate substrates for the enzyme and detecting the resulting reaction product. Finally, simple colorimetric tags may be detected simply by observing the color associated with the tag.

It should be understood that the several features of the blood typing devices of the present invention can be rearranged or modified without altering their function to accommodate different orientations and configurations. For example, the microchannels can each connect several chambers for different purposes, such as a mixing chamber, a reacting chamber, and a viewing chamber. In some embodiments, the microchannels can be shaped to identify the contents of the reservoirs or binding regions. For example, a microchannel connected to a reservoir having anti-A antibodies can be shaped like the letter "A", a microchannel connected to a reservoir having anti-B antibodies can be shaped like the letter "B," and a microchannel connected to a reservoir having anti-D antibodies can be shaped like the letter "D" or the symbol "+." In some embodiments, the microchannels or reservoirs can be directly labeled with the contents of the reservoirs or binding regions.

The various blood typing devices of the present invention are amenable to any suitable modification to augment their function. For example, blood typing devices can further comprise one or more light sources positioned adjacent to the microchannels and are configured to project light through the microchannels. Any agglutination in a microchannel occludes light. In this manner, the presence of any particles of interest in a microchannel can be determined based on the intensity of light shining through. In some embodiments, the blood typing devices can comprise a magnifying lens on the surface of the body adjacent to a microchannel, such that visualization of captured particles on within the microchannel is enhanced. In some embodiments, the blood typing devices can comprise a partially transparent or translucent graphic or chart on the surface of the body adjacent to a microchannel. Light shining through a well can be projected onto the graphic or chart, thereby providing a quick reference indicating which microchannel has captured particles, as well as the identity of the captured particles.

In some embodiments, the blood typing devices can comprise sensors positioned adjacent to a microchannel. Light shining through a microchannel can be detected by, for example, a light or color sensor, which can be supplemented with a computing unit or CPU and a digital readout to display a positive or negative reading for a particle of interest or to quantify the amount of captured particle based on the intensity of light. In some embodiments, the blood typing devices can comprise an impedance sensor or electrode array embedded in a microchannel. An electrode array can also be supplemented with a computing unit or CPU and a digital readout to amperometrically detect the presence or quantify the amount of particles within a microchannel as a measure of impedance. In various embodiments, the computing unit or CPU can be linked to the digital readout by a wired or wireless connection. The digital readout can be incorporated onto a blood typing device, or be on a separate device, such as a desktop, a laptop, a tablet, a cellular phone, a smartphone, or any other device as would be understood by those skilled in the art. In some embodiments, the computing unit or CPU can be located on the separate device, wherein a blood typing device may be inserted into a compatible slot on the separate device and is readable by the separate device like a chip.

The blood typing devices of the present invention can be made using any suitable method known in the art. The method of making may vary depending on the materials used. For example, components of the device comprising a metal may be milled from a larger block of metal or may be cast from molten metal. Likewise, components of the device substantially comprising a plastic or polymer may be milled from a larger block or injection molded. In some embodiments, the devices may be made using 3D printing or other additive manufacturing techniques commonly used in the art.

Method of Use

The present invention also provides methods of determining blood type from a sample of blood. The methods use the portable blood typing devices described herein, the devices having a port fluidly connected to one or more microchannels, each microchannel being fluidly connected to a reservoir containing probes that bind to antigen A, to antigen B, or to antigen D.

In various embodiments, the methods begin with a first step of providing a portable blood typing device of the present invention. In a second step, a blood sample is injected into the port of the device, whereupon the blood sample is drawn into the one or more microchannels. In a third step, each of the breakable seals is ruptured to mix the contents of each reservoir into a fluidly connected microchannel. In a fourth step, the presence of agglutination in each of the microchannels is recorded.

As described elsewhere herein, the blood type of a sample of blood can be determined based on the presence or absence of agglutination in each of the microchannels. For example, in a first combination, the presence of agglutination in a first microchannel downstream from a first reservoir containing a fluid composition comprising a first probe that binds to antigen A and the absence of agglutination in a second microchannel downstream from a second reservoir containing a fluid composition comprising a second probe that binds to antigen B indicates the blood sample contains A-type blood. In a second combination, the absence of agglutination in a first microchannel downstream from a first reservoir containing a fluid composition comprising a first probe that binds to antigen A and the presence of agglutination in a second microchannel downstream from a second reservoir containing a fluid composition comprising a second probe that binds to antigen B indicates the blood sample contains B-type blood. In a third combination, the presence of agglutination in a first microchannel downstream from a first reservoir containing a fluid composition comprising a first probe that binds to antigen A and the presence of agglutination in a second microchannel downstream from a second reservoir containing a fluid composition comprising a second probe that binds to antigen B indicates the blood sample contains AB-type blood. In a fourth combination, the absence of agglutination in a first microchannel downstream from a first reservoir containing a fluid composition comprising a first probe that binds to antigen A and the absence of agglutination in a second microchannel downstream from a second reservoir containing a fluid composition comprising a second probe that binds to antigen B indicates the blood sample contains O-type blood. In any of the first, second, third, and fourth combinations, the presence of agglutination in a third microchannel downstream from a third reservoir containing a fluid composition comprising a third probe that binds to antigen D indicates the blood sample is Rh positive, and the absence of agglutination in a third microchannel downstream from a third reservoir containing a fluid composition comprising a third probe that binds to antigen D indicates the blood sample is Rh negative.

In certain embodiments, the provided portable blood typing device comprises extra functionality that may require additional method steps. For example, the provided portable blood typing device may comprise a light source, whereupon the fourth step can be preceded by a step of activating the light source to facilitate the recordation of agglutination in a microchannel. In another example, the provided portable blood typing may comprise a sensor or electrode array configured to detect agglutination in a microchannel, whereupon the fourth step can be preceded by a step of activating the sensor or electrode array, and the fourth step of recording the presence of agglutination may be performed on a smartphone or other device coupled to the sensor or electrode array by a wired or wireless connection.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A portable blood typing device comprising:
a body having an exterior surface;
a port formed in the exterior surface of the body;
one or more microchannels embedded in the body, each microchannel extending from the port to an air hole formed in the exterior surface of the body; and
one or more reservoirs embedded in the exterior surface of the body arranged in an X array pattern, each reservoir being fluidly connected to each microchannel;
wherein a first reservoir connected to a first microchannel contains a fluid composition comprising a first probe that binds to antigen A, a second reservoir connected to a second microchannel contains a fluid composition comprising a second probe that binds to antigen B, a third reservoir connected to a third microchannel contains a fluid composition comprising a third probe that binds to antigen D, and a fourth reservoir connected to a fourth microchannel contains a fluid;
and wherein the fluid connection between each reservoir and each microchannel is obstructed by a breakable seal.

2. The portable blood typing device of claim 1, wherein the first probe is anti-A antibody, the second probe is anti-B antibody, and the third probe is anti-D antibody.

3. The portable blood typing device of claim 1, wherein the fluid is selected from the group consisting of: gas, air, saline, and phosphate buffered saline.

4. The portable blood typing device of claim 1, wherein each breakable seal is selected from the group consisting of: a foil, a plastic film, a plastic ampoule, and a glass ampoule.

5. The portable blood typing device of claim 1, wherein each breakable seal is breakable by applying pressure to a respective reservoir.

6. The portable blood typing device of claim 1, wherein each breakable seal is breakable by a needle or blade.

7. The portable blood typing device of claim 1, wherein the body is at least partially transparent.

8. The portable blood typing device of claim 1, further comprising one or more magnifying lenses positioned adjacent to a microchannel downstream from a reservoir.

9. The portable blood typing device of claim 1, further comprising one or more light sources positioned adjacent to a microchannel downstream from a reservoir.

10. The portable blood typing device of claim 1, further comprising a blood typing chart attached to the body, the blood typing chart assigning a positive reading based on agglutination in a microchannel downstream from a reservoir and a negative reading based on the absence of agglutination in a microchannel downstream from a reservoir.

11. The portable blood typing device of claim 1, further comprising a sensor electronically connected to a CPU and a display, wherein the sensor automatically detects a positive or negative signal in each microchannel downstream from a reservoir, the CPU assigns a blood type based on the detected signals, and the display shows the blood type.

12. The portable blood typing device of claim 11, wherein the sensor is selected from the group consisting of: a light sensor, an impedance sensor, and a color sensor.

13. A method of blood typing, comprising the steps of:
providing the portable blood typing device of claim 1;
injecting a blood sample into the port;
rupturing each of the breakable seals; and
recording the presence of agglutination in each microchannel downstream from a reservoir.

14. The method of claim 13, wherein the presence of agglutination in a first microchannel downstream from a first reservoir containing a fluid composition comprising a first probe that binds to antigen A and the absence of agglutination in a second microchannel downstream from a second reservoir containing a fluid composition comprising a second probe that binds to antigen B indicates that the blood sample comprises A-type blood.

15. The method of claim 13, wherein the absence of agglutination in a first microchannel downstream from a first reservoir containing a fluid composition comprising a first probe that binds to antigen A and the presence of agglutination in a second microchannel downstream from a second reservoir containing a fluid composition comprising a second probe that binds to antigen B indicates that the blood sample comprises B-type blood.

16. The method of claim 13, wherein the presence of agglutination in a first microchannel downstream from a first reservoir containing a fluid composition comprising a first probe that binds to antigen A and the presence of agglutination in a second microchannel downstream from a second reservoir containing a fluid composition comprising a second probe that binds to antigen B indicates that the blood sample comprises AB-type blood.

17. The method of claim 13, wherein the absence of agglutination in a first microchannel downstream from a first reservoir containing a fluid composition comprising a first probe that binds to antigen A and the absence of agglutination in a second microchannel downstream from a second reservoir containing a fluid composition comprising a second probe that binds to antigen B indicates that the blood sample comprises O-type blood.

18. The method of claim 13, wherein the presence of agglutination in a third microchannel downstream from a third reservoir containing a fluid composition comprising a third probe that binds to antigen D indicates that the blood sample comprises Rh positive blood.

19. The method of claim 13, wherein the absence of agglutination in a third microchannel downstream from a third reservoir containing a fluid composition comprising a third probe that binds to antigen D indicates that the blood sample comprises Rh negative blood.

* * * * *